United States Patent
Jackson et al.

(10) Patent No.: US 6,442,492 B1
(45) Date of Patent: Aug. 27, 2002

(54) CONTROLLING MOISTURE CONTENT OF VAPOR IN CALCINATION OR OXIDATION ZONES

(75) Inventors: Michael K. Jackson, La Grange Park; Michael P. Schumm, Buffalo Grove, both of IL (US)

(73) Assignee: UOP LLC, Des Plaines, IL (US)

( * ) Notice: Subject to any disclaimer, the term of this patent is extended or adjusted under 35 U.S.C. 154(b) by 167 days.

(21) Appl. No.: 09/599,773

(22) Filed: Jun. 22, 2000

(51) Int. Cl.⁷ .................................................. F01P 3/22
(52) U.S. Cl. ........................... 702/31; 702/22; 702/23; 702/24; 702/47; 702/100
(58) Field of Search .............................. 702/22, 23, 24, 702/25, 27, 30–32, 47, 52, 55, 65, 100, 127, 183, 188, FOR 113–115, FOR 115–121, FOR 127–128, FOR 134–135, FOR 170–171; 324/663, 664, 658; 700/266, 273, 274; 62/150

(56) References Cited

U.S. PATENT DOCUMENTS

| | | | |
|---|---|---|---|
| 3,675,442 A | | 7/1972 | Swanson ................. 62/285 |
| 4,100,730 A | * | 7/1978 | Pradt ..................... 60/39.05 |
| 4,197,713 A | | 4/1980 | Bulang .................... 62/94 |
| 4,507,875 A | | 4/1985 | Hirsch et al. .............. 34/44 |
| 4,550,694 A | * | 11/1985 | Evans ..................... 123/41.27 |
| 4,552,570 A | | 11/1985 | Gravatt .................... 95/10 |

(List continued on next page.)

FOREIGN PATENT DOCUMENTS

EP          0 409 546 A2    1/1991    .......... G01N/25/68

OTHER PUBLICATIONS

40 C.F.R. 60, APP. A, Meth. 4.
Process Instruments and Controls Handbook; Considine D.M. Ed. Second Edition, McGraw–Hill; New York pp 5–39 to 5–43.
Instrument Engineers' Handbook, Liptak, B.G. Ed. Revised Edition, Chilton Bok Co.,. Radnor Penn., pp 190–195.
McGraw Hill Encyclopedia of Science and Technology, 6$^{th}$ Edition, McGraw Hill Book Co., New York, p 39.
Product Specification Model 5000 Microprocessor "Level-Lance", Robertshaw Controls Company Tennessee Division.

*Primary Examiner*—Marc S. Hoff
*Assistant Examiner*—Carol S. W. Tsai
(74) *Attorney, Agent, or Firm*—John G. Tolomei; Frank S. Molinaro; Maryann Maas (57) ABSTRACT

A process and apparatus for controlling the amount of water in the vapor of multiple zones of a calcination or oxidation operation have been developed. The process begins with calibration of a vessel housing a capacitance probe. The level of water in a vessel housing the capacitance probe is adjusted so as to immerse from about 5 to about 15 percent of the probe and measuring and recording an initial capacitance, $C_I$. A measured amount of vapor is passed through a condenser, the condensed water is conducted to the vessel and a final capacitance, $C_F$, is measured and recorded. The change in capacitance is calculated, $\Delta C = (C_F - C_I)$, and the difference, $\Delta C$, is used along with the calibration to determine the amount of water condensed. With the amount of water condensed and the measured amount of vapor passed through the vessel, the amount of water in the vapor may be readily calculated. An operating parameter of the calcination or oxidation operation is adjusted to maintain the moisture content in the zones within a predetermined range.

17 Claims, 1 Drawing Sheet

U.S. PATENT DOCUMENTS

| | | | |
|---|---|---|---|
| 4,644,665 A | 2/1987 | Naunapper et al. | 34/389 |
| 4,753,293 A * | 6/1988 | Bohn | 166/267 |
| 4,819,483 A | 4/1989 | Emplit et al. | 73/304 C |
| 4,873,648 A | 10/1989 | Mouser et al. | 364/500 |
| 4,976,210 A | 12/1990 | Dewald | 110/246 |
| 5,103,897 A | 4/1992 | Cullimore et al. | 165/274 |
| 5,123,277 A | 6/1992 | Gray et al. | 73/29.01 |
| 5,332,901 A | 7/1994 | Eckles et al. | 250/345 |
| 5,357,441 A | 10/1994 | Petty et al. | 364/469 |
| 5,456,025 A | 10/1995 | Joiner et al. | 34/528 |
| 5,458,008 A | 10/1995 | Rassat | 73/861.68 |
| 5,544,518 A | 8/1996 | Hart et al. | 73/1 H |
| 5,566,571 A | 10/1996 | Kasai et al. | 73/299 |
| 5,917,078 A * | 6/1999 | Battista et al. | 558/274 |
| 5,966,838 A * | 10/1999 | Krebs et al. | 34/479 |
| 6,042,637 A * | 3/2000 | Weinberg | 96/58 |
| 6,058,619 A * | 5/2000 | Krebs et al. | 34/79 |
| 6,107,215 A * | 8/2000 | Fujimura et al. | 438/798 |

* cited by examiner

CONTROLLING MOISTURE CONTENT OF VAPOR IN CALCINATION OR OXIDATION ZONES

FIELD OF THE INVENTION

The present invention is a process and apparatus for controlling the amount of condensable water in the vapor of multiple calcination or oxidation zones.

BACKGROUND OF THE INVENTION

Moisture control is critical in a great variety of processes, and there are many techniques for measuring the moisture content in vapor. Popular techniques include spectroscopy and dew point sensors which sense a change in electrical capacitance due to condensation on the surface of a probe; see U.S. Pat. Nos. 5,123,277, 5,332,901, 5,357,441, and EP 0409546A2. However, measuring moisture in a vapor atmosphere becomes much more challenging when that atmosphere is at extremely high temperatures such as from 250° C. to 1000° C. At these extreme temperatures, capacitance probes and spectroscopic probes or flow cells fail. An Environmental Protection Agency method resorts to taking a portion of the vapor atmosphere and condensing any water present in the vapor; see 40 C.F.R. 60, App. A, Meth. 4. The amount of water condensed is either weighed or read volumetrically. Measurements by condensing and weighing or reading volumetrically in a graduated cylinder or burette require a significant sample size which may take an extensive period of time to collect. Also, manual weight or volumetric readings lack precision due to the subjectivity of the manual readings.

The present invention provides a technique and apparatus for controlling the moisture of the vapor phase in multiple zones of a high temperature calcination or oxidation operation which eliminate the subjectivity of the manual techniques. The unique design of the apparatus allows for accurate precise moisture measurements on a small sample size and the method of making those measurements provides steps for minimizing error. Furthermore, the small sample size needed allows for rapid determinations of multiple zones of an operation. The application of capacitance measurements as an analytical tool serves to eliminate subjectivity.

SUMMARY OF THE INVENTION

The purpose of the invention is to provide a process and apparatus for controlling the amount of water in the vapor of multiple zones of a calcination or to oxidation operation. The preferred apparatus contains a small volume vessel having a cooled condenser arm and a cooled collection chamber and is further equipped with a capacitance probe having a length extending into the collection chamber of the vessel. The condenser arm is connected to fluid conduits leading to each zone of a multizone calcination or oxidation operation. The process begins with calibrating the equipment and then adjusting the level of water in the collection chamber of a vessel so that from about 5 to about 15 percent of the length of the capacitance probe is immersed in the water and measuring and recording an initial capacitance, $C_I$. A measured amount of vapor from a first zone is passed through the vessel in an amount sufficient to condense water into the collection chamber of the vessel. The vessel is purged with dry air for only such time as necessary to flush any droplets of water retained in the condenser arm of the vessel into the collection chamber of the vessel. A final capacitance, $C_F$, is measured and recorded. The change in capacitance is calculated, $\Delta C = (C_F - C_I)$, and the difference, $\Delta C$, is used along with the calibration to determine the amount of water condensed. With the amount of water condensed and the measured amount of vapor passed through the vessel, the amount of water in the vapor of the first zone may be readily calculated. An operating parameter of the calcination or oxidation process may be adjusted to bring or maintain the amount of water within a predetermined range. The process is repeated for additional zones.

DETAILED DESCRIPTION OF THE INVENTION

Figure 1:
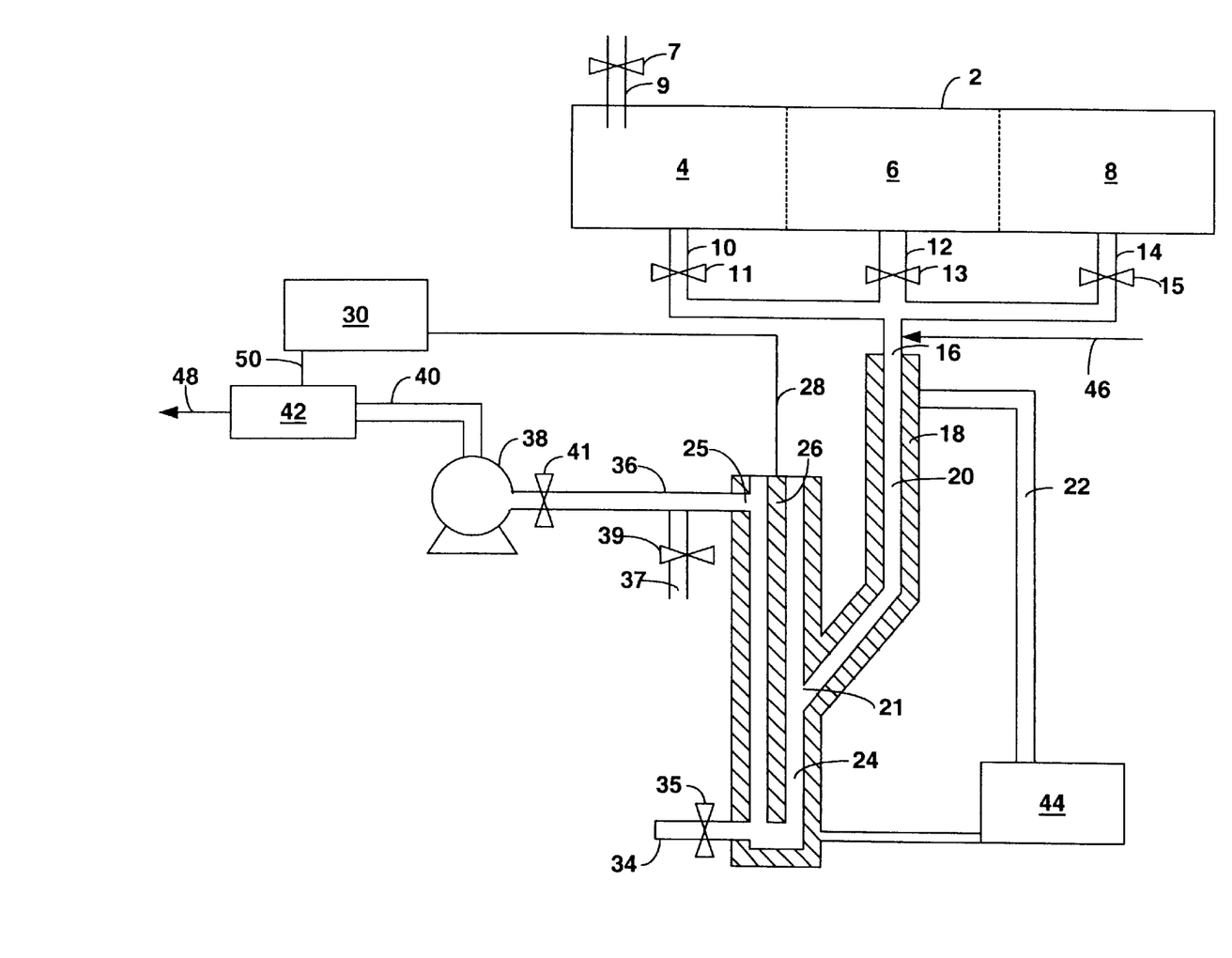
The FIGURE is a schematic representation of the preferred apparatus of the present invention. The figure also depicts an embodiment of the process of the invention that utilizes the preferred apparatus. As to the process, the drawing has been simplified by the deletion of a large number of pieces of apparatus customarily employed in processes of this nature that are not specifically required to illustrate the performance of the invention.

In general terms, the present invention is an accurate and reproducible process for controlling the amount of moisture or water in the vapor atmosphere of different zones of a calcination or oxidation process. It is particularly beneficial due to the high temperatures found in calciners and oxidation units that cause traditional moisture-sensitive probes and devices to fail. Temperatures in these applications can reach up to about 1000° C., well above the operating temperatures of most common moisture analysis devices. Furthermore, the present invention may be equipped to operate in the presence of particulates and/or corrosive compounds (discussed below). Particulates such as catalyst fines are often present in calcination operations, and corrosive compounds such as acids may be present as well.

The process of the invention involves the general steps of calibrating the equipment, obtaining an initial capacitance measurement, sampling a measured portion of the vapor from a first zone, condensing and collecting water from the vapor, obtaining a final capacitance measurement, calculating the amount of water present in the vapor sampled, and adjusting a parameter of the calcination or oxidation operation to maintain the moisture within a predetermined tolerance. The process is not dependent on a unique apparatus, and various different apparatus may be successfully employed. For ease of understanding, the process will be explained below utilizing a preferred apparatus, but such explanation is not intended to limit the broad scope of the invention and it must be emphasized that other apparatus may be used.

The process of the invention begins with calibrating the apparatus. Due to irregularities within the collection vessel, and especially the volume needed for the drain, the apparatus must first be calibrated. Calibration is conducted by adding known amounts of water and taking corresponding capacitance readings. A correlation is developed to correlate the capacitance reading of the probe with the volume of water in the collection vessel. A calibration is needed every time the probe or the collection vessel is changed. The next step is obtaining and recording an initial or zero capacitance measurement which will be discussed in detail below once the preferred general apparatus is explained. A metered portion of the vapor from the first zone to be analyzed is then routed to an apparatus as depicted in the figure. Note that other apparatus may be employed in lieu of the preferred design shown in the figure. A measured amount of the vapor is flowed through the inlet 16 of a condenser arm 20. The vapor may be flowed by such means as vacuum suction and the amount of vapor sampled may be measured using devices such as a rotometer or a wet test meter. The condenser arm is jacketed 18 to provide for coolant to be contacted with and circulated around the condenser arm. Typically, the coolant is pumped using a circulating cooling bath 44. The coolant that is used will depend on the temperature of the vapor entering the condenser arm. For most applications where the condenser arm is to be cooled to a temperature in the range of about 10° C. to about 20° C. suitable coolants include glycols with the preferred glycol being ethylene glycol. As the vapor cools, water is condensed. Depending on the application, other components may be condensed as well as water, and those situations will be discussed later. The geometry of the condenser arm should be such that condensed water cannot collect in the condenser arm. The most preferred geometry is a simple cylindrical or tubular geometry. Some traditional condenser designs may retain condensed water and introduce error into the measurement. It is further preferred that the condenser arm be angled from about 5 to about 30 degrees from the horizontal so that gravity aids in flowing condensed water out of the condenser arm and into a collection chamber. Since the vapor is sampled and cooled prior to contact with a moisture-sensing device, the process is particularly suited to extremely high temperature applications where traditional automated methods fail.

The condensed water and cooled vapor is flowed through the outlet of the condenser arm 21 and into an attached collection chamber 24. The collection chamber is also jacketed to provide for cooling and maintaining a constant temperature in the vessel, and the jacketing is preferably connected to, and a part of, the jacket of the condenser arm. The circulation means and types of coolant are the same as discussed above. The condensed water is collected in the collection chamber, and the moisture-free vapor is allowed to pass through an outlet of the collection chamber 24. The collection chamber is equipped with a capacitance probe 26 to analytically measure the amount of water collected. Capacitance probes have been used to monitor the level of fluid in a vessel since the measured capacitance will change, as a change in the volume of the liquid changes the depth of the probe immersion; see Process Instruments and Controls Handbook; Considine D. M., Ed. Second Edition, McGraw-Hill: New York, pp 5–39 to 5–43, incorporated by reference. However, the capacitance determinations in the present invention are not merely for fluid level monitoring, but are analytical in nature to determine the amount of moisture in a vapor or atmosphere. Capacitance probes are readily available and an example of a suitable probe is the Level-Lance capacitance probe available from the Robert Shaw Company. The capacitance probe extends through the interior of the collection chamber from the upper end of the collection chamber to a location proximate the lower end of the collection chamber. The collection chamber is further equipped with a valved drain 34 located at the lower end of the collection chamber.

The volume within the collection chamber is generally extremely small in comparison with traditional fluid level monitoring capacitance applications. The collection chamber and capacitance probe are preferably sized so that the available volume within the collection chamber will generally accommodate up to about 20 mL of condensed water. It is preferred that the geometry of the interior of the collection chamber conforms to the geometry of the capacitance probe. For example, the most preferred geometry for the capacitance probe is a cylindrical rod, and the most preferred conforming geometry for the interior of the vessel is a cylinder. The collection chamber is further constructed so that the available interior volume for the collection of condensed water is distributed along the length of the probe. For instance, in the preferred case where the capacitance probe is a cylindrical rod and the interior of the vessel is a cylinder, the interior of the vessel would have a small diameter so that volume changes in the condensed water result in large immersion depth changes of the probe and therefore large capacitance changes. In other words, the distance between the interior walls of the collection chamber and the capacitance probe should be minimized so that the interior vessel volume extends along the length of the probe and even small changes in the amount of condensed water collected will result in a reliable capacitance change as measured by the probe. Constructing the collection chamber in this manner allows for the capacitance technique to be employed in an analytical manner to determine the amount of moisture in a vapor. Furthermore, because the total amount of condensed water required for an accurate and reliable measurement is small, less overall vapor needs to be sampled. A small quantity of vapor sampled generally translates into a short time needed to collect the condensed water and take a reading, thereby facilitating timely monitoring and control of the application.

As mentioned earlier, an initial or zero reading must be taken using the capacitance probe before the vapor is sampled and condensed water is added to the collection chamber. According to the present invention, the initial or zero reading is accomplished by first adding water to the collection chamber so that only the lower 5 to 15 percent of the capacitance probe is immersed in the water. After the adjustment to the water level, the probe is allowed to settle for from about 5 seconds to about 90 seconds and then the zero or initial capacitance measurement is taken. The vapor is then sampled, the moisture condensed, and the condensed water collected in the collection chamber as described above. It is preferred that enough vapor be sampled to result in a relatively large change in capacitance readings. It is more preferable that the vapor be sampled until from about 25 to about 95 percent of the length of the capacitance probe is immersed in condensed water, and it is most preferable that the vapor be sampled until from about 50 to about 75 percent of the length of the capacitance probe is immersed in condensed water. When sufficient vapor from the first zone has been sampled, the vapor flow is stopped and a dry air purge is introduced near the inlet of the condenser arm. The purpose of the dry air purge is to force any water droplets that may be adhering to the walls of the condenser arm down into the collection chamber. However, the amount of dry air purge should be only enough to flush residual water through the condenser arm and into the collection chamber. Too much dry air purge could result in evaporation and removal of the condensed water collected in the collection chamber thereby introducing error. The flowrate of the dry air purge should be low enough so as not to unduly disturb or flush out the condensed water in the collection chamber.

After the dry air purge, the capacitance probe is allowed to settle for from about 5 to about 90 seconds and a final or sample capacitance reading is taken. The difference between the initial reading and the final reading, upon calibration correction, is indicative of the amount of condensed water collected. Such calculations are known in the art; see for example Instrument Engineers' Handbook, Liptak, B. G. Ed.

Revised Edition, Chilton Book Co.: Radnor Penn., pp 190–195, incorporated herein by reference. Using the amount of condensed water measured and the amount of vapor sampled, the calculation of the concentration of water that was present in the vapor of the zone sampled is readily performed by one skilled in the art and will not be discussed in detail here. To prepare for the next sampling of the next zone, the collection chamber is drained using the valved drain 34 at the lower end of the vessel. Water is then added to the collection chamber to adjust the level for the zero or initial capacitance measurement as discussed above.

The amount of water determined to be in the vapor of the zone sampled is compared to a predetermined range of acceptable water concentrations. If the amount of water is outside the acceptable range, or is trending in an undesirable direction, an operating parameter of the calcination or oxidation operation may be adjusted. For example, it is common to provide moisture to an oxidation or calcination process via a steam stream. The flow of the steam stream may be increased or decreased so that the moisture levels in the zones of the oxidation or calcination equipment are within acceptable limits. Depending upon the application, the steam feed to each zone may be independently adjusted, or a single steam feed source may be adjusted to modify the overall moisture profile.

It is possible that other components in addition to water may condense in the condenser arm and be collected in the collection chamber of the vessel. For example, compounds such as ammonia, sulfuric acid, and nitric acid may be condensed along with the water. If the amount of condensed material other than water is small or if the additional components do not have a measurable effect on the capacitance measurements, their effect on the overall invention may be negligible in which case no modification of the invention is necessary. If, however, a substantial amount of additional compounds are condensed or if they have a great effect on the capacitance determinations, it may be necessary to calibrate the apparatus to account for the additional components. The mixture of condensable components may be used to perform the calibration and the results of the measurements made using the invention would be considered to be the amount of condensable components in the vapor or atmosphere being sampled in lieu of the amount of water.

The apparatus may be modified to successfully operate in particularly difficult environments. For example, where particulates are present in the vapor to be sampled, a filtering means could be placed in a sampling conduit prior to the condensing arm in order to filter out the particulate matter. Suitable filtering means include quartz wool or glass wool. While the preferred material of construction is stainless steel, where corrosive components such as acids or bases are present, the apparatus may be constructed out of resistant materials such as quartz, plastic or glass. The apparatus also may be connected to a microprocessor and operated automatically with the microprocessor performing such tasks as operating the valves at timed intervals, recording readings and performing the calculations.

Without intending any limitation on the scope of the present invention and as merely illustrative, this invention is explained below in specific terms as applied to a particular embodiment of the invention. First the apparatus )f the invention will be described, and then the process of the invention will tie outlined. Turning now to the figure, a calciner 2 contains three zones, 4, 6, and 3, and each zone is equipped with a valved, 11, 13, 15, vapor conduit 10, 12, and 14, respectively. Steam is introduced to the calciner 2 via conduit 9 having valve 7. Within the calciner, a catalyst is treated at 1000° C., and the moisture of the atmosphere in the calciner is to be determined and monitored over the three zones. Conduits 10, 12, and, 14 are connected to the inlet 16 of condenser arm 20. Condenser arm 20 is jacketed 18 to allow for ethylene glycol coolant to be circulated around condenser arm 20. The coolant is maintained at 100° C. and circulated using cooling bath 44 and line 22. The inlet 16 of condenser arm 20 is further equipped with a dry air purge 46.

A collection chamber 24 is connected to the outlet 21 of condenser arm 20. Collection chamber 24 has an interior that is cylindrical in shape and has a valved 35 drain 34 at the lower end and an outlet 25 at the upper end. Collection chamber 24 is jacketed for cooling with the jacket being connected to and a part of jacket 18 of condenser arm 20. Collection chamber 24 is further equipped with a rod-shaped capacitance probe 26 that extends through the interior of collection chamber 24 from the upper end of the collection chamber to a location proximate the lower end of the collection chamber. Collection chamber 24 and capacitance probe 26 are sized so that the available volume for collection of condensed water is 15 mL, i.e. when the collection chamber 24 contains about 11 mL of condensed water, capacitance probe 26 will be 75 percent immersed in condensed water. Capacitance probe 26 is connected to microprocessor 30 via electrical connection 28. Outlet 25 of collection chamber 24 is connected to vacuum pump 38 via conduit 36 having valve 41. Valved vent line 39 having valve 37 allows for readings to be taken at atmospheric pressure. Vacuum pump 38 is connected to wet test meter 42 via conduit 40. Wet test meter 42 is equipped with vent conduit 48 and electrical communication line 50.

The process of the invention begins with calibrating the equipment. Irregularities in the shape of collection vessel 24, especially near drain 35 and outlet 21 result in the actual volume increments to be non linear with resulting incremental changes in capacitance. Therefore, known incremental volumes of water are added to collection vessel 24 and with each incremental volume of water, the capacitance is recorded. A correlation is developed that relates the capacitance change to the actual increase in the volume of water. Typically, the calibration will begin at a specific volume of water that is sufficient to submerse the lower-most 15 percent of the capacitance probe 26, and then, as discussed below, prior to each moisture analysis that same volume of water is added.

After the calibration is complete, any water in collection chamber 24 is drained using drain 34 and valve 35. Fresh water is then added to collection chamber 24 so that the lower-most 15 percent of capacitance probe 26 is immersed in fresh water. Capacitance probe 26 is allowed to settle during a fifteen-second pause. An "initial" capacitance measurement is taken using capacitance probe 26 and the "initial" capacitance value is recorded via microprocessor 30. A first vapor sample is then conducted by vacuum suction from zone 4 via open valve 11 and conduit 10 to inlet 16 of condenser arm 20. Valves 13 and 15 would now be closed. As the vapor passes through condenser arm 20, water is condensed. Both the remaining vapor and the condensed water are flowed though the outlet 21 of condenser arm 20 and into collection chamber 24 where the condensed water is collected. The vapor exits collection chamber 24 through outlet 25 and is conducted via line 36 to a vacuum pump which provides the vacuum suction needed to sample the vapor in the calciner. Vapor exiting the vacuum pump is conducted via line 40 to wet test meter 42 where the flowrate of the vapor is measured. The elapsed time for the vapor sampling is also measured, and both the elapsed time and the flowrate are communicated to microprocessor 30 via line 50.

The vapor being analyzed is continuously flowed through the condenser arm and collection chamber until about 11 mL of condensed water has been collected in collection chamber 24; it is preferred to collect from about 2 to about 15 mL of condensed water. The vapor flow is discontinued, and a dry air purge 46 is begun. Dry air purge 46 forces droplets of condensed water adhering to the interior of the condenser arm into the collection chamber. For the configuration and sizing of this example, the dry air purge is continued for a period of from about 30 seconds to about 1 minute. Care must be taken so that the dry air purge does not evaporate the collected water. After the dry air purge is discontinued, the condensed water and capacitance probe 26 are allowed to settle during a 30-second pause. Valve 41 is closed and valve 39 is opened to allow for the capacitance measurement to be taken at atmospheric pressure. A "final" capacitance measurement is taken using capacitance probe 26 and the "final" capacitance value is recorded via microprocessor 30. Within microprocessor 30 the initial capacitance value is compared to the final capacitance value to calculate the change in capacitance due to the volume of condensed water in the collection chamber. The change in capacitance is then used along with the calibration correlation to determine the amount of condensed water that was collected from the first zone, and from the amount of water collected, the amount of water present in the vapor of the first zone sampled is calculated using known mathematical formulas or algorithms. An operating parameter of zone 4 or of the calcination process in general may then be adjusted so that the amount of water in the vapor of the first zone is within a predetermined tolerance. For example, valve 7 may be adjusted to increase or decrease the amount of steam that is fed through line 9 into zone 4.

The process is then repeated to measure the moisture in zone 6 of calciner 2. As before, the condensed water from the previous analysis is completely drained from collection chamber 24 using drain 34. Fresh water is added so that the lowermost 15 is percent of capacitance probe 26 is immersed in water. Capacitance probe 26 is allowed to settle during a 30-second pause. An "initial" capacitance measurement is taken using capacitance probe 26 at atmospheric pressure and the "initial" capacitance value is recorded via microprocessor 30. However, for this analysis, the vapor sample is conducted by vacuum suction from zone 6 via open valve 13 and conduit 12 to the inlet se 16 of condenser arm 20. Valves 11 and 15 are closed. The process continues as discussed above to determine the moisture concentration in zone 6 of calciner 2. An operating parameter of zone 6 or of the calcination process in general may then be adjusted so that the amount of water in the vapor of the zone is within a predetermined tolerance. With respect to the Figure, line 9 feeds steam to the whole calciner and therefore valve 7 may be adjusted to increase or decrease the amount of moisture in zone 6.

In this application, the process would be repeated a third time to measure the moisture in zone 8 of calciner 2 by sampling the vapor from zone 8 via open valve 15 and line 14. Valves 11 and 13 would be closed. An operating parameter of zone 8 or of the calcination process in general may then be adjusted (such as valve 7 of steam line 9) so that the amount of water in the vapor of the last zone is within a predetermined tolerance. After the three iterations of the process the results together would provide an overview of the moisture content across the calciner and indicate the particular moisture values in each of the zones. An overall moisture control may be accomplished by adjusting operating parameters and monitoring the overview of the moisture content across the three zones of the calciner. It is expected that each analysis would be completed in less than fifteen minutes so that through continuous sequential sampling of the zones one may monitor and control the moisture content of the vapor in the zones of the calciner over time and throughout the calcination operation.

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, applying the invention to an oxidation operation, using different probe configurations, and different cooling devices can be readily extrapolated from the foregoing description.

EXAMPLE

A measured amount of dry air and a measured amount of water were heated to form steam. The amount of water taken up by the air was measured by manual readings of the volume changes of a burette. The concentration of water in the steam was determined by 1) condensing the water into a graduated cylinder and manually reading the volume of condensed water and 2) using the method and apparatus of the present invention as described above with the exception of the initial or zero capacitance reading step. For the following experiments, the initial or zero capacitance reading was performed with no water being present in the collection chamber. In all of the tables below the "burette" column shows the amount of water dispensed into the flowing dry air to form the steam, the "graduated cylinder" column shows the amount of water condensed from the steam and collected and manually read in a graduated cylinder, and the "present invention" column shows the determination as made using the present invention with the exception noted above. In TABLE 1 the steam was introduced directly to the condenser arm, while in the rest of the tables the steam flowed through a complete vapor-sampling route. In all cases the burette was set to dispense water at 0.7 mL/min, and the vapor was allowed to flow for from 2 to 5 minutes. The calculation of the theoretical amount of water present in the steam is shown as the duration of time the air was flowed multiplied by the flowrate of 0.7 mumin. The results of the experiments are shown in the following tables. The data demonstrates the repeatability of the process and the apparatus of the present invention.

TABLE 1

3 minute duration × 0.7 mL/min. = 2.1 mL of water in steam

| Trial No. | Burette | Graduated Cylinder | Present Invention |
|---|---|---|---|
| 1 | 2.1 | 2.1 | 1.84 |
| 2 | 2.2 | 2.4 | 1.85 |
| Mean | 2.15 | 2.25 | 1.845 |
| Standard Deviation | 0.0707 | 0.2121 | 0.0070 |

TABLE 2

3 minute duration × 0.7 mL/min. = 2.1 mL of water in steam

| Trial No. | Burette | Graduated Cylinder | Present Invention |
|---|---|---|---|
| 1 | 2.2 | 2.3 | 1.77 |
| 2 | 2.2 | 2.3 | 1.77 |
| 3 | 2.2 | 2.2 | 1.75 |
| 4 | 2.2 | 2.3 | 1.84 |
| 5 | 2.2 | 2.2 | 1.76 |
| Mean | 2.2 | 2.26 | 1.778 |
| Standard Deviation | 0.0 | 0.0547 | 0.0356 |

TABLE 3

3 minute duration × 0.7 mL/min. = 2.1 mL of water in steam

| Trial No. | Burette | Graduated Cylinder | Present Invention |
|---|---|---|---|
| 1 | 2.2 | 2.2 | 1.77 |
| 2 | 2.2 | 2.3 | 1.77 |
| 3 | 2.2 | 2.4 | 1.75 |
| 4 | 2.2 | 2.2 | 1.84 |
| 5 | 2.3 | 2.3 | 1.76 |
| Mean | 2.22 | 2.28 | 1.946 |
| Standard Deviation | 0.0447 | 0.0836 | 0.0944 |

TABLE 4

4 minute duration × 0.7 mL/min. = 2.8 mL of water in steam

| Trial No. | Burette | Graduated Cylinder | Present Invention |
|---|---|---|---|
| 1 | 3.0 | 2.7 | 2.46 |
| 2 | 2.9 | 2.8 | 2.47 |
| 3 | 2.8 | 3.0 | 2.70 |
| 4 | 2.9 | 2.8 | 2.50 |
| 5 | 2.9 | 2.8 | 2.48 |
| Mean | 2.9 | 2.82 | 2.522 |
| Standard Deviation | 0.0707 | 0.1095 | 0.1005 |

TABLE 5

5 minute duration × 0.7 mL/min. = 2.8 mL of water in steam

| Trial No. | Burette | Graduated Cylinder | Present Invention |
|---|---|---|---|
| 1 | 3.7 | 3.7 | 3.46 |
| 2 | 3.7 | 3.7 | 3.47 |
| 3 | 3.6 | 3.6 | 3.26 |
| 4 | 3.7 | 3.6 | 3.20 |
| 5 | 3.7 | 3.6 | 3.14 |
| Mean | 3.68 | 3.64 | 3.306 |
| Standard Deviation | 0.0447 | 0.0547 | 0.1512 |

What is claimed is:

1. An apparatus for controlling the amount of condensable water in the vapor of at least two calcination or oxidation zones comprising:
   a) fluid conduits from each zone of a calcination or oxidation apparatus, the conduits equipped with valves and a gas meter;
   b) a condenser arm having an inlet and an outlet for the condensation of water in a vapor, the inlet of the condenser arm attached to the fluid conduits;
   c) a collection chamber attached to the outlet of the condenser arm and having:
      i) an upper end and a lower end,
      ii) an interior volume defined by interior walls,
      iii) an outlet at the upper end,
      iv) a drain at the lower end,
      v) a capacitance probe extending through the interior volume from the upper end to a point proximate the lower end without contacting the interior walls, where said interior volume and capacitance probe are sized so that up to about 20 mL of water can be contained within the collection chamber; and
   d) a jacket encasing both the condenser arm and the collection chamber to define a volume through which coolant is passed cooling both the condenser arm and the collection chamber.

2. The process of claim 1 wherein the vapor is initially at a temperature ranging from about 250° C. to about 1000° C.

3. The process of claim 1 wherein the purge with dry air in step (f) is for about 30 to about 60 seconds.

4. The process of claim 1 further comprising recording the capacitance and performing the calculations using a microprocessor.

5. The process of claim 1 further comprising removing particulates from the vapor prior to passing the vapor through the condenser.

6. The process of claim 1 wherein the measured amount of vapor is sufficient to immerse the lower 25 to 95 percent of the probe in condensed water.

7. The process of claim 1 further comprising condensing other compounds along with the water.

8. The process of claim 1 further comprising periodically repeating the steps (b) through (k) to control the amount of condensable water in the vapor of the N zones over time.

9. The process of claim 1 wherein the pausing of steps (d) and (g) is for a time ranging from at least 5 seconds to about 95 seconds.

10. The process of claim 1 wherein the operating parameter adjusted is the flow of steam to the oxidation or calcination operation.

11. An apparatus for controlling the amount of condensable water in the vapor of at least two calcination or oxidation zones comprising:
    a) fluid conduits from each zone of a calcination or oxidation apparatus, the conduits equipped with valves and a gas meter;
    b) a condenser arm having an inlet and an outlet for the condensation of water in a vapor, the inlet of the condenser arm attached to the fluid conduits;
    c) a collection chamber attached to the outlet of the condenser arm and having:
       i) an upper end and a lower end,
       ii) an interior volume defined by interior walls,
       iii) an outlet at the upper end,
       iv) a drain at the lower end,
       v) a capacitance probe extending through the interior volume from the upper end to a point proximate the lower end without contacting the interior walls, where said interior volume and capacitance probe are sized so that up to about 20 mL of water may be contained within the collection chamber; and
    d) a jacket encasing both the condenser arm and the collection chamber to define a volume through which coolant is passed cooling both the condenser arm and the collection chamber.

12. The apparatus of claim 11 wherein the geometry of the collection chamber conforms to the geometry of the capacitance probe.

13. The apparatus of claim 11 wherein the condenser arm has a cylindrical geometry and is positioned at an angle of about 5 to about 30 degrees from the horizontal.

14. The apparatus of claim 11 wherein the condenser arm and the collection chamber are constructed of stainless steel.

15. The apparatus of claim 11 wherein the condenser arm and the collection chamber are constructed of a material selected from the group consisting of quartz, glass, and plastic.

16. The apparatus of claim 11 further comprising a filtering means for removing particulates attached to the inlet of the condenser arm.

17. The apparatus of claim 16 wherein the means for removing particulates is glass wool or quartz wool.

* * * * *

UNITED STATES PATENT AND TRADEMARK OFFICE
CERTIFICATE OF CORRECTION

PATENT NO.    : 6,442,492 B1
DATED         : August 27, 2002
INVENTOR(S)   : Jackson et al.

It is certified that error appears in the above-identified patent and that said Letters Patent is hereby corrected as shown below:

<u>Column 9, lines 55 through Column 10, line 12,</u>
Please replace Claim 1 with the following:

1. A process for controlling the amount of condensable water in the vapor of at least two calcination or oxidation zones comprising:
a) calibrating a capacitance probe housed in a collection vessel by adding known amounts of water to the collection vessel at atmospheric pressure, reading the capacitance of the probe, and developing a correlation between the volume of water in the collection vessel and capacitance of the probe;
b) draining the collection vessel housing the capacitance probe;
c) introducing liquid water into the collection vessel so as to immerse the lower 5 to 15 percent of the probe;
d) pausing for at least five seconds, and measuring and recording the capacitance, $C_I$;
e) flowing a measured amount of vapor from calcination or oxidation zone N, where N is an integer from 1 to at least 2, to a condenser and passing condensed water into the collection vessel;
f) purging the condenser with dry air for only such time as necessary to flush any droplets of water retained in the condenser into the collection vessel;
g) pausing for at least five seconds and measuring and recording the capacitance, $C_F$, at atmospheric pressure;
h) calculating the amount of condensed water from the difference of $C_F - C_I$, from the calibration correlation;
i) determining therefrom the amount of condensable water in the vapor of the calcination or oxidation zone N;

UNITED STATES PATENT AND TRADEMARK OFFICE
CERTIFICATE OF CORRECTION

PATENT NO. : 6,442,492 B1
DATED : August 27, 2002
INVENTOR(S) : Jackson et al.

It is certified that error appears in the above-identified patent and that said Letters Patent is hereby corrected as shown below:

j)      adjusting an operating parameter of the calcination or oxidation operation to achieve or maintain the amount of water in the vapor of zone N within a predetermined tolerance; and k)      repeating steps (b) through (j) for additional zones, N.

Signed and Sealed this

Seventeenth Day of December, 2002

JAMES E. ROGAN
*Director of the United States Patent and Trademark Office*